(12) United States Patent
Lopez et al.

(10) Patent No.: US 6,251,438 B1
(45) Date of Patent: Jun. 26, 2001

(54) METHOD OF PREPARING ACTIVE SUBSTANCES FROM NACRE, PRODUCTS OBTAINED WHICH CAN BE USED IN PARTICULAR AS MEDICAMENTS

(75) Inventors: Evelyne Lopez, Paris; Michel Giraud, Melgven; Sophie Berland, Taverny; Christian Milet, Saint-Pierre-lès-Nemours; Gilles Gutierrez, Lyons, all of (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 09/091,989
(22) PCT Filed: Dec. 27, 1996
(86) PCT No.: PCT/FR96/02098
 § 371 Date: Oct. 16, 1998
 § 102(e) Date: Oct. 16, 1998
(87) PCT Pub. No.: WO97/24133
 PCT Pub. Date: Jul. 10, 1997

(30) Foreign Application Priority Data

Dec. 28, 1995 (FR) .................................. 95 15650

(51) Int. Cl.$^7$ ................................... A61K 35/56
(52) U.S. Cl. .................... 424/547; 424/115; 424/520
(58) Field of Search ................. 424/195.1, 115, 424/520, 547

(56) References Cited

FOREIGN PATENT DOCUMENTS 2 715 568  8/1995  (FR) .

OTHER PUBLICATIONS

Lopez et al. Tissue & Cell. vol. 24(5) pp. 667–679, (1992).*
Silve et al. Calcified Tissue International vol. 51(5) pp. 363–369, (1992).*

* cited by examiner

Primary Examiner—Leon B. Lankford, Jr.
(74) Attorney, Agent, or Firm—Foley & Lardner

(57) ABSTRACT

This invention relates to a method for preparation of biologically active substances and has the following characteristic features: (a) nacre is reduced to a powder whose grain size is less than approximately 200 $\mu$m; (b) it is placed in close contact with an aqueous solvent, (c) at the end of the contact period, the insoluble fraction is separated out to give the aqueous fraction; (d) the solvent of the aqueous fraction is concentrated to separate out the soluble or water-transportable fraction of the nacre, which is made up of biologically active substances with essentially no mineral components. The invention likewise relates to the products obtained by this method, their use for medicinal purposes and the compositions containing them.

15 Claims, No Drawings

METHOD OF PREPARING ACTIVE SUBSTANCES FROM NACRE, PRODUCTS OBTAINED WHICH CAN BE USED IN PARTICULAR AS MEDICAMENTS

The present invention relates to a method of preparing biologically active substances from nacre and to the uses of the purified products which can be obtained in this way.

These products are, in particular, useful in bone and, in particular, maxillofacial surgery, or for the treatment of degenerative pathologies of the cartilage, as well as in dermatology.

Nacre has been proposed as a material for bone substitution and/or regeneration, in particular in orthopedic or maxillofacial surgery, and also for the manufacture of dental implants.

It has furthermore been shown (Lopez et al., Tissue and Cell, 24, 667–679, 1992) that nacre exerted, at a distance, osteoinducing and osteogenic effects on bone cells in vitro.

It was therefore desirable to be able to isolate the biologically active substances present in nacre.

It is known that nacre, or aragonite chonchylifer, is a biogenic mineralized formation; it consists of an organic matrix of fibrous and non-fibrous substances representing about 1.7% of the total mass (Taylor et al., Bulletin of the British Museum (Natural History) Zoology, Suppl. 3. 125 pp. +29 plates, 1969) and calcium carbonate crystallized in the form of aragonite. The structure of nacre therefore exhibits similarities with that of bone, which comprises an organic matrix and a mineral phase, consisting of calcium phosphate in the form of hydroxyapatite. In contrast, about 50% of the organic matrix of nacre is soluble.

Authors have described the extraction of proteins which are active on the formation of bone, BMPs (or Bone Morphogenetic Proteins) from the insoluble fraction of the matrix of bone (Urist et al., Proc. Natl. Acad. Sci. USA 76: 1828–1832, 1979). This method involves an acidic demineralization, which entails the risk of denaturing the products of interest.

Although nacre has for a long time been suggested as a biomaterial, proteins similar to BMPs, for example, have never been demonstrated.

Applicant has now found a method making it possible to separate substances having a set of particularly beneficial biological properties, in particular because it does not include a denaturing step.

This is why the present invention relates to a method for preparing biologically active substances from nacre, characterized in that:

a) nacre is reduced to a powder whose particle size is less than about 200 $\mu$m (that is to say in general from 50 to 150 $\mu$m), b) this is brought into intimate contact with an aqueous solvent, optionally supplemented by salts, c) at the end of the contact period, the insoluble fraction is separated so as to recover the aqueous fraction, d) the solvent of the aqueous fraction is concentrated so as to recover the soluble or water-transportable fraction of the nacre, which consists of biologically active substances essentially free of mineral constituents.

This method is one which is simple to employ, and is preferably carried out at a temperature of between about 4° C. and 30° C.; good results are obtained at room temperature.

The nacre used may be obtained from shells of molluscs, in particular oysters such as *Pinctada maxima*. Raw nacre is used, which is free of other calcite-rich shell elements; the starting material is preferably white nacre, otherwise a step of removing the pigments must be provided.

This is a readily available raw material, the use of which does not impact negatively on natural populations; indeed, most of these oysters or other nacrous molluscs are farmed.

Furthermore, an additional advantage is given by the fact that the raw material can be obtained from oyster shells which have produced pearls; indeed, a pearl oyster is removed from the productive pool after having produced at most 3 pearls in succession, even though it has a thick layer of nacre of excellent quality (grade A). The present invention therefore provides an extra opportunity for using nacre downstream of pearl farming.

The nacre can be used without prior decontamination. The purified biological fractions extracted from nacre originating from bivalves filtering on a large scale (800 l water/day) are free of pathogenic agents which may be active in man, which constitutes an essential part of the conditions for an implantable biomaterial, for which harmlessness in the short and long term is currently a major preoccupation. This preoccupation is justified by the concern to avoid the serious pathologies which may occur through the use of lyophilized bone, for example in bone surgery.

In one of the embodiments of the method, the nacre is reduced to a particle size of between 50 and 100 $\mu$m.

In another embodiment, the nacre is reduced to a powder with particle size between 15 and 50 $\mu$m, which makes it possible to improve efficiency by approaching the size of a crystalline unit.

In all cases, crushing will firstly be carried out, followed by grinding, since a one-off size reduction procedure is not suited to the consistency of the starting material.

The solvent in step b) may be selected from pure, double-distilled or apyrogenic water, or water supplemented by salts selected, in particular, from NaCl or guanidine hydrochloride.

The invention has in fact made it possible to demonstrate that the substances responsible for the biological activity of nacre are hydrophilic or transportable in water, in particular water-soluble, and can be extracted as early as the first fractionation step, on condition that finely reduced nacre is treated, which limits its production cost.

The product which can be obtained directly by the method defined above comprises a mixture of proteins which have biological activities stimulating cell proliferation, in particular of osteoblasts, chondrocytes, keratinocytes and fibroblasts. These proteins may or may not be fibrous. The invention relates not only to the product obtained in this way, but also to the various substances purified by fractionation from the complete soluble product.

It comprises in particular proteins which may be likened to ancestral proteins associated with the BMP/TGF $\beta$ (transforming growth factor) family.

More particularly, the invention relates to one or more non-fibrous osteoinducing proteins which can be obtained from nacre and have the following characteristics:

they are soluble in water or are transportable in water, they are non-cytotoxic, they increase the alkaline phosphatase activity and the type I collagen synthesis by the osteoblasts.

It also relates to nucleotide sequences coding for a protein of this type. It should therefore be understood that proteins of this type, obtained from another source or by in vivo synthesis, by isolated tissues or organs or by cells in culture are also included in the invention, as are products obtained by chemical synthesis or genetic engineering.

The biologically active product may be concentrated in step d) by dialysis and/or lyophilization.

In one variant of the method, after step d), precipitation with ethanol is carried out and the residue which will constitute a biologically active sub-fraction is recovered, the products which remain in solution constituting another biologically active sub-fraction.

Step b) may, in particular, be carried out by suspending the nacre powder in the aqueous solvent under mechanical agitation; one possibility is to carry out the procedure at 4° C. for 24 hours, but the times and temperatures may be adapted by the person skilled in the art, for example according to the starting particle size.

In another embodiment, step b) is carried out by passing the solvent under pressure through the nacre powder which is rendered imobile. This immobilization is, for example, brought about using a column of the HPLC type, optionally as a mixture with filler substances allowing better solvent diffusion and avoiding compacting of the nacre powder.

The various products obtained according to the invention are useful as an implant or medicament, in particular intended to increase the regeneration of tissues, in particular osseous, cartilaginous or cutaneous tissues.

There are many fields of application, including:
Various tissues:
   skeletal tissues: bone, cartilage, ligaments, teeth, cement, ivory and the many others,
   cutaneous and subcutaneous tissues,
   the many others.
Various pathologies:
   degenerative aging, traumatic, tumoral, aesthetic and handicap,
   rheumatological infections, including arthrosis, polyarthritis, etc.
   orthopedic infections (traumatologies and for corrective purposes),
   calcium metabolism pathologies,
   dermatological or dermatocosmetological infections,
   or the like.

The products according to the invention may, in particular, be used in surgery, interventional radiology or any other treatment techniques.

Various modes of application may be envisaged, generally or locally, with a view to an immediate action effect or with a view to delayed action effect.

The products and proteins according to the invention may be included in pharmaceutical compositions. These may be in various forms, such as: solutions, suspensions, lyophilizates, powders, gels, pastes, adhesives, viscous, nonviscous, coatings, casts, etc.

They may also, for example, be used in the following cases:
For interventions under imaging
   local bone repair (lose of substance) or diffuse bone repair (demineralization); in the spine, the limbs (compact bone, spongy bone), the flat bones of the face and the skull, the thoracic skeleton or the like.
   cartilage repair, intervertebral discs and articular surfaces, for example following damage of the arthrosic or traumatological type, or the like.
Treatment of various pathologies of the skeletal tissues in all cases mentioned above, in conventional surgery manufacture of bespoke bone grafts in vitro, by stimulation of osteoblasts or fibroblasts (osteo-induction).
Treatment of dermatological pathologies
   by local application
   by surgical intervention (injection, graft or the like) after in vitro production of skin grafts In the case of autografting of bone cells, for contributing to stimulating and maintaining the phenotype expression of human bone-forming cells (osteoblasts) in culture. These autologous osteoblasts are intended to be re-implanted in the form of an autograft.

"per os" use with a view to the regulation of calcium metabolism.

According to an advantageous aspect, the composition furthermore contains a biocompatible solid support; this will be doped by adding biologically active products in a defined amount. The composition may be used as a filler material, to make it possible to repair the skeleton in the event of a loss and/or lack of bone substance, whether of traumatological, aesthetic or pathological nature.

According to another aspect, the composition contains excipients suitable for cutaneous administration. It may induce cicatrization and skin regeneration.

The invention also relates to the production of antibodies targeted against the various biologically active protein fractions, it being possible for these antibodies to be labeled with radioactivity, fluorescence, chromogenic reagent or enzymatically.

It relates to the production of labeled or unlabeled probes.

According to another aspect, the invention relates to diagnosis kits containing an antibody and a probe as defined above.

The products and proteins according to the invention may be included in cosmetic compositions intended in particular to combat the effects of aging.

Lastly, the invention comprises the use of hydrosoluble substances and proteins which can be extracted from nacre as cell culture additives, as well as culture media containing them.

EXAMPLE I

Extraction

*Pinctada maxima* nacre in the form of irregular fragments (supplied by the company EVM Développement, SARL, 5, rue Capron. 75018 PARIS.SIRET 38348098500019) is washed in running water then by three applications of distilled water. These fragments are converted into micronized form, with a particle size between 50 and 100 $\mu$m. The powder obtained is decontaminated with $\gamma$-rays and extracted, without prior demineralization, by mechanical agitation at 4° C. for 24 hours, using double-distilled pure water or apyrogenic water or a 25 g/l strength solution of NaCl or an aqueous solution of guanidine hydrochloride (pH 7.4). A soluble fraction is obtained after vacuum filtration, concentrated by lyophilization then dialyzed against water using a membrane having a diameter of 40 mm and a porosity of from 12,000 to 14,000 Daltons. A part of the fraction obtained in directly lyophilized. The other part is precipitated with ethanol (24 hours at 4° C.).

The set of operations carried out is summarized in the following diagram:

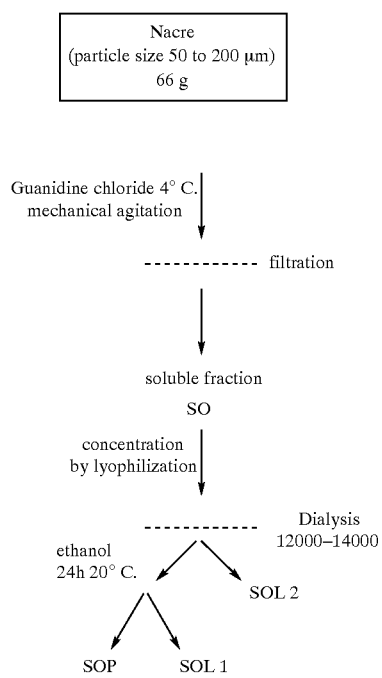

Fractionation, analysis of the proteins and peptides.

The U.V. absorption spectra and the chromatographic analysis of the raw fractions show that these fractions are essentially of protein or peptide nature.

The principal steps of fractionating the organic matrix into its various constituents use, in combination, the conventional techniques of high pressure liquid chromatography (HPLC) and electrophoresis. Size exclusion (SEC), ion exchange (IEX), hydrophobic interactions (HIC), hydroxyapatite (HPHT) and affinity chromatography (AFC) are the most common HPLC methods. These methods are regarded as not denaturing proteins or peptides, and therefore not causing an impairment in biological activity.

The electrophoretic techniques for analyzing proteins are capillary zone electrophoresis at high pH (CZE), analytical electrophoresis and preparative electrophoresis. All these electrophoresis methods have high resolution and do not denature.

EXAMPLE 2

In vitro biological tests

Experimental biological material

Human osteoblasts, chondroblasts, fibroblasts and keratinocytes in culture. First-run cells from individuals of different sex and variable age (child–adult–elderly).

Evaluation criteria used
1) Cytotoxicity, the proliferation and migration of the cells is evaluated using the MTT test, a colorimetric technique based on the conversion of the tetrazolium salt (yellow) into a formazan salt (blue-violet) by the NADPH reductase of living cells.
2) Stimulation of the activity of osteoblasts maintained in confluence, evaluated by increasing presence and/or alkaline phosphatase activity.
3) Synthesis of collagen of type I by the osteoblasts, type II by the chondrocytes, and type III by the fibroblasts. These collagens, constituents of the peptide extracellular matrix, are indicators of the activity of these cell types.
4) Synthesis of chondroitin sulfate and hyaluronic acid, constituents of the non-peptide extracellular matrix secreted by the chondrocytes.
5) Calcium fixation (mineralization process) on the extracellular organic matrix synthesized by the osteoblasts (evaluated by atomic absorption spectrophotometry).
6) Synthesis of PTHrp by the keratinocytes.

By way of example:

Activity of the Fractions: test of activity on human osteoblasts in culture

| Extract | MTT Difference relative to control | Alkaline P. Difference relative to control | Type I collagen expression |
|---|---|---|---|
| SOP | + | + | +++ |
| SOL 1 | + | NS | +++ |
| SOL 2 | + | + | ++ |

NS = not significant

Determination of the components of the organic matrix on the basis of extracts;

Immunodetection after electrophoresis and transfer on membrane—on the basis of raw extract—

| Type I collagen | Type II collagen | Type III collagen | Decorin | PTHrp | CGrp |
|---|---|---|---|---|---|
| +++ | ++ | + | + | + | + |

EXAMPLE 3

In vivo: evaluation criteria used

Demonstration of the activity of the fractions: the SAMPATH test (SAMPATH et al., 1990) used for characterizing the biological activity (osteoinduction) of Bone Morphogenetic Proteins (BMPs) is chosen as the model.

| Subcutaneous site total nacre (powder) | Type II collagen[1] Immunolocalization | Type I collagen[2] Immunolocalization | Alkaline phosphatase[3] Activity test |
|---|---|---|---|
| 1 week | + | − | − |
| 2 weeks | + | + | + |
| 4 weeks | − | + | + |

[1]: specific to cartilage
[2]: majority in bone
[3]: osteoblast activity

Demonstration of the activity on skin regeneration: by local application to wounds (scars, burns or the like) induced in animals (rat, rabbit).

|  | Induced skin wound (rat) | |
| --- | --- | --- |
|  | Control Sham operated | + Total nacre application (powder) |
| Chronic inflammation | + | − |
| Cicatrization at D + 2 | ± | +++ |

What is claimed is:

1. A method for preparing biologically active substances, comprising the steps of:
   a) reducing nacre to a powder whose particle size is less than about 200 µm,
   b) contacting said powder with an aqueous solvent to produce an insoluble fraction and an aqueous fraction,
   c) separating the aqueous fraction from the insoluble fraction,
   d) concentrating the aqueous fraction so as to recover the soluble or water-transportable fraction of the nacre, which contains biologically active substances essentially free of mineral constituents.

2. The method according to claim 1, wherein in in step a), the nacre is reduced to a particle size of between 50 and 100 µm.

3. The method according to claim 1, wherein in in step a), the nacre is reduced to a powder with particle size between 15 and 50 µm.

4. The method according to claim 1, wherein in step b), the solvent is selected from the group consisting of pure, double-distilled or apyrogenic water, and water supplemented by salts.

5. The method according to claim 1, wherein in step d), concentration is followed by dialysis and/or lyophilization.

6. The method according to claim 1, further comprising: e) contacting the water soluble or water transportable fraction of d) with ethanol so as to produce a sub-fraction containing said biologically active substances.

7. The method according to claim 1 wherein step b) is carried out by suspending the nacre powder in the aqueous solvent under mechanical agitation.

8. The method according to claim 1 wherein step b) is carried out by passing the solvent under pressure through the nacre powder which is rendered immobile.

9. A product obtained by the method according to claim 1.

10. A pharmaceutical composition, comprising at least one product according to claim 9, wherein said product is soluble in water, is non-cytotoxic, and increases the alkaline phosphatase activity and the type I collagen synthesis by osteoblasts.

11. The pharmceutical composition according to claim 10, further comprising a biocompatible solid support.

12. the composition according to claim 10, further comprising excipients suitable for cutaneous administration.

13. A cosmetic composition comprising at least one product obtainable by the method of claim 1.

14. A cell culture medium, comprising at least one product according to claim 9, wherein said product is soluble in water, is non-cytotoxic, and increases the alkaline phosphatase activity and the type I collagen synthesis by osteoblasts.

15. The method of claim 4, wherein said salts are either NaCl or guanidine hydrochloride.

* * * * *